(12) United States Patent
Maiden et al.

(10) Patent No.: US 8,318,179 B2
(45) Date of Patent: Nov. 27, 2012

(54) NEISSERIAL VACCINES

(75) Inventors: Martin Maiden, Oxford (GB); Ian Feavers, Wheathamstead (GB); Andrew Pollard, Oxford (GB)

(73) Assignee: ISIS Innovation, Ltd., Oxford (GB)

( * ) Notice: Subject to any disclaimer, the term of this patent is extended or adjusted under 35 U.S.C. 154(b) by 1295 days.

(21) Appl. No.: 11/628,106

(22) PCT Filed: Jun. 3, 2005

(86) PCT No.: PCT/GB2005/002207
§ 371 (c)(1),
(2), (4) Date: Nov. 29, 2006

(87) PCT Pub. No.: WO2005/117956
PCT Pub. Date: Dec. 15, 2005

(65) Prior Publication Data
US 2007/0224222 A1    Sep. 27, 2007

(30) Foreign Application Priority Data
Jun. 3, 2004  (GB) .................................. 0412407.9

(51) Int. Cl.
A61K 39/116    (2006.01)
A61K 39/00     (2006.01)
A61K 39/095    (2006.01)
A61K 45/00     (2006.01)

(52) U.S. Cl. ............... 424/203.1; 424/184.1; 424/250.1; 424/249.1; 424/278.1

(58) Field of Classification Search .................. None
See application file for complete search history.

(56) References Cited

U.S. PATENT DOCUMENTS

| | | | |
|---|---|---|---|
| 7,118,757 B1 | 10/2006 | Seid | |
| 2003/0224012 A1 | 12/2003 | Ruelle | |
| 2006/0110412 A1* | 5/2006 | Desmons et al. | 424/250.1 |
| 2007/0087017 A1* | 4/2007 | Olivieri et al. | 424/250.1 |

FOREIGN PATENT DOCUMENTS

| | | |
|---|---|---|
| WO | WO 94/25596 | 11/1994 |
| WO | WO 96/31618 | 10/1996 |
| WO | WO 00/78966 | 12/2000 |
| WO | WO 2004/020463 | 3/2004 |
| WO | WO 2005/117956 | 12/2005 |

OTHER PUBLICATIONS

Thompson et al. (Microbiology, 2003; 149: 1849-1858).*
Luijkx et al. (Infection and Immunity, 2003; 71(11): 6367-6371.*
Malorny et al. (Journal of Clinical Microbiology, 1996; 34(6): 1548-1550).*
Feavers et al., Clinical and Diagnostic Laboratory Immunology, vol. 3, pp. 444-450 (1996).
Jodar et al., The Lancet, vol. 359, pp. 1499-1508 (2002).
Peeters et al., Vaccine, vol. 17, pp. 2702-2712 (1999).
Pollard et al., Archives of Disease in Childhood, vol. 87, pp. 13-17 (2002).
Russell et al., Emerging Infectious Diseases, vol. 10, pp. 674-678 (2004).
Urwin et al., Infection and Immunity, vol. 72, pp. 5955-5962 (2004).

* cited by examiner

*Primary Examiner* — Vanessa L Ford
*Assistant Examiner* — Lakia Tongue
(74) *Attorney, Agent, or Firm* — Elliot M. Olstein; Alan J. Grant

(57) ABSTRACT

The present invention relates to compositions comprising at least one purified PorA protein antigen and at least one purified FetA protein antigen. In particular, said PorA/FetA antigens are antigenically variable antigens comprising the variable regions of PorA/FetA. Specific combinations of PorA/FetA epitopes are presented for example in Table 3. The invention also relates to methods of immunization comprising administering said compositions, and to methods for producing compositions. Preferably the compositions are purified protein compositions. Preferably the compositions are vaccine compositions.

22 Claims, 3 Drawing Sheets

NEISSERIAL VACCINES

This application is a national phase of International Application Serial No. PCT/GB2005/002207, filed 3 Jun. 2005, which claims priority of British Application Serial Number 0412407.9, filed 3 Jun. 2004, the disclosures of which are hereby incorporated by reference in their entirety.

FIELD OF THE INVENTION

The invention relates to vaccine compositions and to their design. In particular the invention relates to vaccine compositions for protection against N. meningitidis, including protection against N. meningitidis serogroup B.

BACKGROUND OF THE INVENTION

Neisseria meningitidis, a common commensal inhabitant of the human nasopharynx, is a major cause of bacterial meningitis and septicaemia worldwide. Acapsulate meningococci are essentially avirulent and only five of the thirteen chemically and immunologically distinct meningococcal capsular polysaccharides, which define meningococcal serogroup, are frequently associated with invasive disease. Although protein-polysaccharide conjugate vaccines offer the possibility of protection against meningococcal disease caused by serogroups A, C, Y and W135, this approach has not been successful for serogroup B meningococci. Furthermore, comprehensive prevention does not appear possible with polysaccharide-based vaccines alone. Problems arise from the fact that the serogroup B polysaccharide structure is poorly immunogenic. Further problems arise due to its similarity to sialylated glycopeptides on human cells.

Prior art vaccines have often made use of purification of so called "blebs" which represent vesicles shed from the cell surface of the particular organism of interest. However, such a crude product carries many problems. For example, there is wide variation in the composition of these blebs. There is no reliable way of controlling which proteins are included or excluded from these blebs. These blebs may or may not include polysaccharide-coating elements of the organism of interest. The proportions of the various components of the blebs in relation to one another cannot be reliably determined. The composition of these blebs cannot be easily determined or controlled.

Many attempts have been made to develop vaccines based on the sub-capsular antigens, especially the outer membrane proteins (OMPs). Meningococcal OMPs are highly diverse and, although OMP-containing outer membrane vesicle (OMV) vaccines have been effective against the particular epidemic strain from which they were made, levels of potentially cross-protective immune responses to heterologous strains have been disappointing.

One prior art vaccine is the so called OMV (outer membrane vesicle) vaccine. This has included up to nine different PorA proteins. This nine fold vaccine is made up of OMVs produced from three different strains of bacterium, each bearing its naturally occurring PorA plus two further PorA's which have been engineered into each of the three strains. This is the so called "conventional" vaccine. As such, it suffers from similar problems are as present in other parts of the prior art such as are associated with vesicle vaccines generally. These problems include difficulty in controlling the levels of antigen present, the difficulties associated with the fact that this is a vesicle based vaccine and include the crude nature of the preparation used.

OMV vaccines containing outer membrane proteins (OMPs) have been used in the control of epidemics caused by single strains in Norway and Cuba. Due to the high antigenic diversity of many OMPs among different strains, immune responses to vaccines of this type are usually limited to the strains used in their manufacture or their close relatives. Consequently, this approach does not provide effective control of endemic serogroup B disease, which is attributed to diverse strains.

Feavers et al 1996 (Clinical and Diagnostic Laboratory Immunology Volume 3 pp 444-450) discusses the antigenic diversity of the meningococcal PorA outer membrane protein. A wide ranging serological and nucleic acid typing study is described. Medical problems presented by antigenic variability are discussed in relation to vaccine design. Although PorA protein vaccines are mentioned, they are mentioned in the context of illustrating the problems associated with the design of protein component vaccines directed against a variable antigen. Indeed, the unpredictability of these vaccines is discussed, and the efforts towards identification of conserved antigens are summarised.

Thompson et al 2003 (Microbiology Volume 149 pp. 1849-1858) reports extensively on the antigenic diversity of the meningococcal FetA protein. FetA is shown to be very highly diverse. Out of 107 individual N. meningitidis isolates examined, 60 different FetA alleles were identified. These 60 alleles encoded 56 different FetA protein sequences. Thompson et al explained that the diversity of this FetA protein will compromise its effectiveness as a vaccine component. Indeed, it is thought to be present in certain outer membrane vesicle (OMV) vaccines, but these vaccines suffer from the problem of strain specificity. Indeed, in order to expand the coverage of protection using OMV vaccines, OMVs derived from each invasive genotype predominant in a particular area would be needed to be included in vaccine formulations. The conclusions reached in Thompson et al are that FetA is so diverse it is likely to be largely ineffective in vaccine formulations and that conserved antigens probably offer the best way forward in vaccine development.

The present invention seeks to overcome problem(s) associated with the prior art.

SUMMARY OF THE INVENTION

The present invention is based on the surprising finding that antigenically variable antigens can be exploited in vaccinating to provide broad protection against a range of different strains of the target organism. Previously, antigenically variable antigens were considered to be a very poor candidate component for vaccine compositions due to their variability and various other difficulties which have been outlined above. Variable antigens have previously only been considered suitable for strain-specific vaccination. However, as explained in detail herein, the deep analysis of the phylogeny of these various variable antigens has surprisingly revealed that certain combinations of said antigens may be exploited in combination to provide an effective vaccine composition.

In particular, in the field of meningococcal vaccines, the combination of PorA and FetA antigens is found to be particularly advantageous due to the very similar immune responses elicited by each antigen individually. These responses are not only similar in nature but also similar in strength. These advantageous properties allow immunodominance effects to be easily removed from vaccine compositions as described herein.

Furthermore, and most importantly, the invention is based on deeper insights into the representation of PorA and FetA antigens across the extremely broad range of antigenically diverse meningococcal isolates which have been studied. It is surprisingly shown that selection of a relatively small number of variable antigens from PorA and from FetA combined, can provide protection against an extremely broad range of those disease associated isolates.

Thus in a first aspect the invention relates to a composition comprising at least one purified PorA protein antigen and at least one purified FetA protein antigen. It is surprisingly shown herein that the antigenically variable regions of these proteins can be used in compositions, preferably vaccine compositions, providing broad protective coverage. Preferably the PorA/FetA antigens are antigenically variable antigens comprising the variable regions of PorA/FetA.

The variable regions of PorA/FetA are characterised and epitopes have been described within those regions. As is discussed in more detail below, combinations of those variable epitopes can be exploited to provide effective vaccine compositions despite the variability of the epitopes. The epitopes are listed in Table 3. Preferably the composition comprises at least one PorA VR1 epitope and at least one PorA VR2 epitope, wherein said epitopes are selected from the list presented in Table 3. Preferably the composition comprises at least one FetA epitope selected from the list presented in Table 3.

Certain defined combinations of epitopes advantageously provide protection against specific groups of disease causing isolates. Often these combinations/groupings will be determined by the operator. Some particularly advantageous combinations are presented below.

In one aspect the invention relates to a composition as described above wherein the composition comprises PorA epitopes P1.5-2, P1.10, P1.7 and P1.13-1 and FetA epitopes F5-1 and F1-5. This provides a core protection. Preferably the composition further comprises PorA epitopes P1-20 and P1.9, and FetA epitope F3-1. This is especially useful in protection against African/Asian isolates.

In one aspect the invention relates to a composition wherein the composition comprises PorA epitopes P1.5-1, P1.2-2, P1.5-2, P1.16, P1.5, P1.10, P1.7, P1.7-2 and P1.4, and FetA epitopes F1-5, F5-1 and F3-9. This provides an extended core protection. Preferably the composition further comprises PorA epitopes P1.13-1, P1-20 and P1.9, and FetA epitopes F3-1 and F5-5.

This advantageously provides a 'standard' vaccine having more than 88% coverage of global isolates. Preferably the composition further comprises PorA epitopes P1.19 and P1.15. This advantageously provides an 'enhanced' vaccine having more than 90% coverage of global isolates.

In another aspect, the invention relates to an extended core composition as described above wherein the composition further comprises PorA epitopes P1.2, P1.19 and P1.15, and FetA epitope F1-7. This advantageously provides a composition, preferably a vaccine composition, directed to protection against European/USA isolates.

In another aspect, the invention relates to a composition as described above wherein the composition comprises PorA epitopes P1.5 and P1.2 and FetA epitopes F3-6 and F5-1. This advantageously provides protection directed at the ST-11 complex isolates.

In another aspect, the invention relates to a composition as described above wherein the composition comprises PorA epitopes P1.7, P1.16, P1.19 and P1.15 and FetA epitope F3-1. This advantageously provides protection directed at the ST-32 complex isolates.

In another aspect, the invention relates to a composition as described above wherein the composition comprises PorA epitopes P1.7-2 and P1.4 and FetA epitopes F1-5 and F1-7. This advantageously provides protection directed at the ST-41/44 complex isolates.

Additional components may be used to advantageously included in the composition(s) in order to supplement the immune responses generated. Preferably the compositions described above further comprise one or more components selected from the group consisting of transferrin binding proteins, PorB, Opa, NspA. Preferably said further component is selected from the group consisting of transferrin binding protein, PorB and Opa. Preferably said further component is Opa.

Preferably the composition is a purified protein composition.

Preferably the composition is a vaccine composition.

In another aspect, the invention relates to methods of immunising a subject against *Neisseria meningitidis* infection comprising administering to said subject an effective amount of a composition, preferably a vaccine composition, as described above.

In another aspect, the invention relates to methods of inducing an immune response against *Neisseria meningitidis* in a subject comprising administering to said subject an effective amount of a composition, preferably a vaccine composition, as described above.

In another aspect, the invention relates to a method of producing a vaccine composition against an organism comprising the steps of:—
  (i) providing surface protein sequences for said organism;
  (ii) selecting from said surface proteins those which are antigenically variable;
  (iii) determining the incidence of each of said antigenically variable proteins in clinical occurrences of said organism;
  (iv) selecting a sub-group of antigens from said antigenically variable surface proteins to provide optimal representation of different isolate(s) of the organism whilst including the minimum number of individual antigens; and
  (v) providing the antigens selected in step four in a vaccine composition.

The compositions may advantageously be balanced to avoid immunodominance effects. Thus, preferably the individual antigens for inclusion in the composition are further selected as inducing equivalent immune responses. The compositions may advantageously be produced to cover as many disease related strains as possible. Thus, preferably said antigens are further selected to be representative of variation between multiple disease associated strains of said organism.

In one embodiment, the number of antigens included in a composition may be limited or predetermined. In this embodiment, step (iv) of the above method would simply be adapted to selecting a sub-group of antigens from said antigenically variable surface proteins to provide maximal representation of different isolate(s) of the organism whilst including the predetermined number of individual antigens.

In another embodiment, the coverage of the composition may be predetermined for example to a geographical spread or to a particular clone or collection of isolates. In this embodiment, step (iv) of the above method would simply be adapted to selecting a sub-group of antigens from said antigenically variable surface proteins to provide the desired coverage by choosing a single antigen providing the greatest possible increase in coverage and adding this to the sub-group of selected antigens until addition of a further antigen would not further increase the coverage of isolate(s) of the organism.

In some embodiments, a so-called 'multiple hit' approach may be used. A 'single hit' approach is where at least one antigen present on each covered isolate is included in the composition. A multiple hit approach is where multiple antigens present on each covered isolate are included in the composition, such as a 'double-hit' approach where at least two antigens per isolate are included. In general, multiple hit approaches are preferred.

In another aspect the invention relates to a composition comprising a combination of PorA and FetA epitopes as set out in Table 3. Preferably said composition comprises a combination of PorA and FetA epitopes as described above. Preferably said composition is a vaccine composition. Preferably said composition is an outer membrane vesicle vaccine.

Preferably compositions according to the present invention are essentially free from cellular components such as polysaccharide capsule material and/or vesicles. This provides the advantage that the compositions are free from additional antigens which are not intended to be present but can be carried by cellular debris. Furthermore, it facilitates the regulatory approval process since the compositions according to the present invention preferably do not contain cellular fractions which can be less predictable in their composition and therefore give rise to problems of consistency and batch variation, which problems are advantageously avoided by using purified protein only compositions as described herein.

DETAILED DESCRIPTION OF THE INVENTION

Meningococcal Diversity

In addition to antigenic diversity, meningococcal populations are genetically highly diverse; many genotypes have been identified by the examination of housekeeping genes that are subject to stabilising selection for conservation of metabolic function. These genotypes have been identified as electrophoretic types (ETs) by multi-locus enzyme electrophoresis (MLEE) and more recently as sequence types (STs) by multi-locus sequence typing (MLST). Population studies that exploit MLEE and MLST have identified equivalent groups of related genotypes referred to as 'clonal complexes'; these are now named after a predominant, or central, ST, e.g. ST-1 complex, and include all isolates that share identical alleles with this ST at four or more MLST loci. Isolate collections corresponding to populations of asymptomatically carried meningococci show greatest genetic diversity with less diversity present in collections of disease-associated meningococci. The latter are dominated by meningococci belonging to a limited number of clonal complexes known as the hyper-invasive lineages.

OMP Diversity

It is well established that meningococcal OMPs are highly diverse in peptide sequence and that their genes are subject to strong positive selection in regions encoding those parts of the proteins exposed to immune attack. The strength of positive selection recorded in the porB gene, for example, exceeds that reported for the envelope protein of HIV-1. These observations raise the possibility of poor efficacy and the rapid spread of escape variants following the introduction of vaccines that include meningococcal OMPs as immunodominant constituents. There is, however, some evidence for structure in the extent of antigenic diversity present in meningococcal populations and, if understood and exploited, these limitations could simplify vaccine design and implementation.

Associations of particular serotypes (PorB variants) and serosubtypes (PorA variants) with clonal complex have been identified in several studies, and variants observed in PorA VR1 and VR2 are structured into non-overlapping combinations. Both of these associations appear to be maintained in the face of diversifying selection and high rates of recombination that both reassort genes among clonal complexes and generate mosaic genes encoding novel antigen variants. In addition, a study of antigenic variants of the OMP TbpB in the ST-5 complex indicated that whilst antigenic variants emerged during epidemic spread, they were less fit than the parent genotype and lost during subsequent transmission.

PorA/FetA

PorA and FetA are outer membrane proteins of *N. meningitidis*. Their sequence composition is well known to a person skilled in the art. The variable regions of these proteins have been mapped and are described in the literature. For convenience, reference is made to "neisseria.org" which is a central resource in which sequence information is available for both FetA and PorA. Each variable region comprises at least one epitope. The terms 'variable region' and 'epitope' are sometimes used interchangeably herein as will be apparent from the context. This is explained in more detail below.

The variable region sequences (ie. epitope sequences) of both proteins are classified according the accepted scheme known in the art and the common numerical designations for the different sequence variants are used throughout this document (see for example Russell et al 2004 Emerging Infectious Diseases vol. 10 p 674).

Preferably the term 'antigenically variable antigen' refers to an antigen comprised by variable region(s) ('VR') of the particular protein concerned.

FetA has a single variable region (epitope sequence). The sequences of all known variants of this variable region are known in the art. For convenience, reference is made to the list of FetA VR sequences at http://neisseria.org/nm/typing/feta/vr.shtml.

PorA has two variable regions (epitope sequences), VR1 and VR2. The sequences of all known variants of these two variable regions are known in the art. For convenience, reference is made to the list of PorA VR1 sequences at WWW.neisseria.org/nm/pora/vr1, and the list of PorA VR2 sequences at WWW.neisseria.orq/nm/pora/vr2 PorA antigens described herein preferably comprise one VR1 and one VR2 per PorA protein. Many VR1/VR2 sequence combinations are known in nature, and those combinations which are not known in nature may be easily constructed by a person skilled in the art using elementary recombinant molecular biology techniques to put the relevant VR1 and VR2 sequences together in a PorA context as required. Where PorA epitope compositions are given as VR1, VR2, preferably these two epitopes are provided on a single PorA protein. However, where more than one PorA protein is comprised by a particular composition, then the list of epitopes for that particular composition is more important than the particular pairings on any one PorA molecule. For example, if P1.5-1, 2-2, P1.5-2,16 is specified, this will include combinations of PorA molecules such as (P1.5-1,2-2 and P1.5-2,16) as well as combinations such as (P1.5-1,16 and P1.5-2,2-2) or supersets which include each of the listed epitopes. Preferably the PorA epitope combinations are provided as written ie. if P1.5-1,2-2, P1.5-2,16 is specified then preferably the PorA is provided as (P1.5-1,2-2 and P1.5-2,16).

Preferably the compositions only comprise the specified PorA/FetA epitopes.

PorA and FetA are protective and generate bactericidal responses in both humans and animal models of infection and protection. In the prior art, PorA has been a major constituent of strain-specific vaccines included in vaccine trials or in development. While FetA has been included in prior art strain specific vaccines and is protective, it is relatively less exploited as it is not expressed well in vitro. The PorA VRs, especially VR2, and the FetA VR are similar in that they are relatively long surface-exposed peptides (VR2 ranges from 8-24 amino acids long; FetA VR ranges from 20-42 amino acids long) that are easily defined.

Antigen Combinations

Preferably antigens are chosen to provide similar overall immune responses.

For example antigens providing similar immunogenic properties are particularly suitable for combination. Proteins having well defined variable regions are especially suitable for use in the present invention. Particularly good combinations of antigens are found when the individual antigens produce very similar immune responses. Especially advantageous are antigens having a similar strength of immune response since this helps to remove immunodominant effects. Antigens inducing a similar quality of immune response are also good candidates for combination. For example, if each of the antigens elicits an immune response with known bactericidal activity then this is again advantageous. If this bactericidal activity is found at similar levels for the different antigens, then they are even better suited to combination. In summary, the closer the match between immune responses (in terms of the quality and/or quantity) generated by two different antigens, the better candidates they are for combination.

The FetA-PorA combination is particularly advantageous since the PorA variable regions are more similar in their immunogenic properties to the FetA immunogenic regions than to other outer membrane proteins considered.

Similar criteria can be applied to a selection of particularly advantageous third or further components of vaccine compositions according to the present invention. This is discussed in more detail herein.

Further advantages of the PorA-FetA combination include the exceptionally broad coverage which it is possible to achieve with inclusion of the minimal number of individual protein antigens.

Compositions

It is disclosed herein that a combination of PorA and FetA variants in a composition, preferably a vaccine composition, can be particularly effective given the strong structuring of bacterial populations expressing immunogenic variants of these two antigens. The survey of 78 isolates (see examples) showed that as few as 6 PorA variants (P1.5-1,2-2, P1.5-2,16, P1.5,10, P1.7,13-1, P1.7-2,4, P120,9) combined with 5 FetA variants (F1-5, F3-1, F5-1, F3-9, F5-5) would provide homologous protection against all 78 isolates. This combination of PorA and FetA antigenic variants according to the present invention protects against 95 of the 107 (89%) diverse meningococcal isolates used to develop MLST from which the 78 representative of the hyper-invasive lineages were derived.

Form of the Antigens

Antigens may be used in any suitable form such as purified protein or nucleic acid encoding the antigens. The antigens are preferably used in the form of purified protein antigens. The term 'purified' in this context means essentially free from cellular components such as polysaccharide capsule material and/or vesicles. Preferably the antigens are used in the form of essentially homogeneous protein preparations as judged by coomassie stained SDS-PAGE.

Clearly, a purified preparation of one antigen mixed with a purified preparation of another antigen to produce a composition, preferably a vaccine composition, gives rise to a mixture of at least two polypeptide species which mixture itself will not be homogeneous since it will comprise at least two antigen species. Thus, a composition comprising purified X and purified Y will be understood to be 'purified' in the sense explained above ie. that it will be essentially free from cellular components such as polysaccharide capsule material and/or vesicles. The mere presence in the overall composition of different individual elements X and Y does not mean that those elements are no longer 'purified' by virtue only of having been combined as described.

Preferably the antigens are produced by recombinant means. Preferably the antigens are produced in the absence of *N. meningitidis*, such as production by recombinant means in a non-*N. meningitidis* cell. Preferably the antigens are produced via expression in *E. coli*.

The production of the individual purified antigens is within the ability of the person skilled in the art. These can be produced by any suitable means known in the art, for example by recombinant expression, purification and refolding (if necessary) in vitro such as described in Idanpaan-Heikkila, I., Wahlstrom, E., Muttilainen, S., Nurminen, M., Kayhty, H., Sarvas, M., and Makela, P. H. (1996) Immunization with meningococcal class 1 outer membrane protein produced in *Bacillus subtilis* and reconstituted in the presence of Zwittergent or Triton X-100 Vaccine 14: 886-891; Jansen, C., Kuipers, B., van der, B. J., de Cock, H., van der, L. P., and Tommassen, J. (2000) Immunogenicity of in vitro folded outer membrane protein PorA of *Neisseria meningitidis* FEMS Immunol. Med. Microbiol. 27: 227-233; Jansen, C., Wiese, A., Reubsaet, L., Dekker, N., de Cock, H., Seydel, U., and Tommassen, J. (2000) Biochemical and biophysical characterization of in vitro folded outer membrane porin PorA of *neisseria meningitidis* [In Process Citation] Biochim. Biophys. Acta 1464: 284-298; Qi, H. L., Tai, J. Y., and Blake, M. S. (1994) Expression of Large Amounts of Neisserial Porin Proteins in *Escherichia coli* and Refolding of the Proteins into Native Trimers. Infection and Immunity 62: 2432-2439.

Antigens may be concatenated ie. physically joined for example by production of multiple antigens by expression as a continuous polypeptide chain. In one embodiment, this may be accomplished using genetically engineered hybrids of PorA and FetA expressing epitopes from both proteins. For example, the semi-variable cell-surface loop five of PorA may be replaced with the VR from FetA, such that a PorA-FetA fusion protein is produced comprising not only the PorA VR1 and VR2 but also the FetA VR. The choice of epitopes for this type of concatenation or fusion protein follows the details described herein according to the desired protection sought. This approach advantageously reduces the number of physical proteins required to provide the same level of cross-protection.

In any case, concatenation of epitopes may be carried out for simple convenience/optimisation of the production process, or for other reasons such as balancing of the induced immune response. Preferably only antigens inducing similar strength responses are concatenated onto single polypeptides. Preferably concatenation is only performed for antigens occurring within a particular protein. Preferably concatenation is avoided. Preferably individual purified antigens are prepared and stored separately until needed to produce a composition according to the present invention.

The precise amounts of individual antigens in particular vaccine compositions will typically be determined by the person working the invention. Preferably equimolar amounts of individual antigens are used. More preferably the amounts used are balanced with regard to the strength of immune response induced against a particular antigen species. Thus, if an antigen elicits a response at only half the strength of a reference antigen, then twice the molar amount of that antigen should be used. Similarly, if an antigen elicits a response at twice the strength of the reference antigen, then approximately half the molar amount should be used. Preferably the optimal relative proportions and dosage levels are determined by clinicians/clinical studies.

This balancing advantageously helps to avoid immunodominance effects produced by inequalities between the individual antigen components of the vaccine compositions. This process can be seen as a simple process of titration towards an end-point of even response against each of the antigens in a given vaccine composition, preferably of even protection against each of the antigens in a given vaccine composition. The titration is preferably performed by a serum bactericidal antibody assay or an ELISA.

Optimisation

Clearly, the best vaccine may well be the vaccine having broadest coverage. However, to obtain the broadest coverage may require the inclusion of the greatest number of antigens into the vaccine composition. Therefore, preferably a balance is struck between minimising the number of antigens included in the composition and maximising the coverage of protection which might be afforded by said composition. These are the factors which should govern the choice of antigens in the present invention.

In more detail, the first antigen to be chosen would be the single antigen which occurred in the greatest number of individual isolates of the organism of interest. This single antigen would provide the greatest coverage across those isolates. When considering what to choose as a second antigen, attention should be paid to those isolates which are not yet represented by inclusion of the first antigen. In this manner, the second antigen should be chosen to provide the greatest coverage across those so far unrepresented isolates. At this point, two antigens will have been selected. These will have been selected to provide the best coverage possible for the selection of only two antigens. However, there may still be a group of isolates which are not yet represented. Therefore, the choice of the third antigen should address those isolates which have not yet been represented. This iterative process of choosing and selecting antigens should be continued to achieve as high a level of coverage in terms of the number of isolates covered as possible. Preferably the process should be continued until each of the known isolates is covered.

Advantageously, if all isolates are covered yet there is still space in the composition for inclusion of further antigens, the above process may be continued selecting further antigens which will provide further immunological responses against the maximum number of isolates. In this way, dual responses may be generated against individual isolates. This is sometimes called the 'double hit approach'. Clearly, the more responses which are generated against each isolate, the better chance of providing protective response in the host subject. Therefore, greater numbers of antigens and greater numbers of hits against each isolate are preferred. However, practical difficulties including considerations of cost in preparation of the composition dictate some limitation on the number of antigens included in that particular vaccine composition. This limitation will vary from application to application. Furthermore, using fewer antigens will almost always result in an easier to produce and ultimately cheaper vaccine composition. Furthermore, there may be technical advantages to reducing the number of vaccines in the compositions such as elimination of immunodominance effects, ease of balancing the responses, and/or simplification of administration. The actual limitation on the number of antigens included in a particular composition is not important to the invention. The important principle is that when choosing the antigens they are chosen according to the process outlined above, that is to say an iterative process in which maximising the coverage of protection is given the highest priority. In this way, whatever the actual numerical limitation on the number of antigens included in a particular vaccine composition, a vaccine composition containing that limited number of antigens will always provide the greatest possible coverage when the antigens are selected according to the present invention.

Thus in one aspect the number of antigens to be included in a particular composition will be determined before the choice of individual antigens is made. Each individual antigen is then chosen as explained above, maximising the coverage attained with the addition of each individual antigen to the composition, preferably the vaccine composition.

In another aspect, the coverage of a particular composition will be determined before the number of antigens to be included in the composition is determined. Each individual antigen is then chosen as explained above, adding antigens one at a time until the desired coverage is attained.

Naturally, many compositions may involve a compromise between a desired coverage and a preferred limitation on the number of antigens included in the composition. The present invention advantageously enables such factors to be balanced by following the guidance given herein.

In general, the fewer antigens the composition comprises, the simpler and cheaper it will be to manufacture, administer and monitor. Therefore in some aspects a low number of antigens will be advantageous.

In aspects of the invention when a composition is designed by coverage, then clearly a greater number of antigens may be desirable in order to attain that coverage and the general preference for a smaller number of antigens will be balanced to allow the desired coverage to be attained.

The vaccine composition may comprise twenty antigens or even more. Preferably, the vaccine composition will comprise eighteen or fewer antigens, preferably sixteen or fewer antigens, preferably fourteen or fewer antigens, preferably twelve or fewer antigens, preferably eleven or fewer antigens, preferably ten or fewer antigens, preferably nine or fewer antigens, preferably eight or fewer antigens, preferably seven or fewer antigens, preferably six or fewer antigens, preferably five or fewer antigens, preferably four or fewer antigens, preferably three or fewer antigens, preferably the vaccine composition comprises two antigens.

The definition of an antigenically variable antigen (as compared to an antigenically conserved antigen) is well known in the art for example a variable antigen is one which differs by one or more amino acids from the sequence of the prototype antigen. As a result of this sequence difference it is likely to elicit an antibody response that is less than 100% cross-reactive between the variant and the prototype. Variable antigens will be characterised by predominance of non-synonymous over synonymous nucleotide substitutions.

Further Components

The compositions and/or vaccine formulations of the present invention comprise at least one purified PorA antigen and at least one purified FetA antigen. These vaccine compositions may advantageously be supplemented with further component(s) to improve the vaccines eg. to improve their efficacy.

This third or further component may advantageously be selected from transferrin binding proteins, PorB, opacity associated adhesins (Opas), NspA, *N. meningitidis* cell surface components such as outer membrane protein(s) or other entity capable of eliciting or augmenting an immune response. Preferably the third or further component is an outer membrane protein. Preferably the third or further component is selected from the list consisting of transferrin binding proteins, PorB, Opas.

Vaccine Formulations

The present invention provides a pharmaceutical/vaccine composition comprising a therapeutically effective amount of the PorA/FetA epitopes of the present invention and a pharmaceutically acceptable carrier, diluent or excipient (including combinations thereof).

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be administered using a mini-pump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be administered by a number of routes.

Where the agent is to be administered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

PorA/FetA protein may be prepared in situ in the subject being treated. In this respect, nucleotide sequences encoding said protein may be delivered by use of non-viral techniques (e.g. by use of liposomes) and/or viral techniques (e.g. by use of retroviral vectors) such that the said protein is expressed from said nucleotide sequence.

Administration

The term "administered" includes delivery by viral or non-viral techniques. Viral delivery mechanisms include but are not limited to adenoviral vectors, adeno-associated viral (AAV) vectors, herpes viral vectors, retroviral vectors, lentiviral vectors, and baculoviral vectors. Non-viral delivery mechanisms include lipid mediated transfection, liposomes, immunoliposomes, lipofectin, cationic facial amphiphiles (CFAs) and combinations thereof.

The components of the present invention may be administered alone but will generally be administered as a composition—e.g. when the components are is in admixture with a suitable pharmaceutical excipient, diluent or carrier selected with regard to the intended route of administration and standard pharmaceutical practice.

For example, the components can be administered in the form of tablets, capsules, ovules, elixirs, solutions or suspensions, which may contain flavouring or colouring agents, for immediate-, delayed-, modified-, sustained-, pulsed- or controlled-release applications.

If the administration is via a tablet, then the tablet may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavouring agents, colouring matter or dyes, with emulsifying and/or suspending agents and with diluents such as water, ethanol, propylene glycol and glycerin, and combinations thereof.

The routes for administration (delivery) include, but are not limited to, one or more of: oral (e.g. as a tablet, capsule, or as an ingestable solution), topical, mucosal (e.g. as a nasal spray or aerosol for inhalation), nasal, parenteral (e.g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, vaginal, epidural, sublingual.

In a preferred aspect, the composition is delivered by injection.

It is to be understood that not all of the components of the composition need be administered by the same route. Likewise, if the composition comprises more than one active component, then those components may be administered by different routes.

If a component of the present invention is administered parenterally, then examples of such administration include one or more of: intravenously, intra-arterially, intraperitoneally, intrathecally, intraventricularly, intraurethrally, intrasternally, intracranially, intramuscularly or subcutaneously administering the component; and/or by using infusion techniques.

For parenteral administration, the component is best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

As indicated, the component(s) of the present invention can be administered intranasally or by inhalation and is conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A™) or 1,1,1,2,3,3,3-heptafluoropropane (HFA 227EA™), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of the agent and a suitable powder base such as lactose or starch.

The component(s) of the present invention may also be dermally or transdermally administered, for example, by the use of a skin patch.

It will be understood that these regimes include the administration of the substances sequentially, simultaneously or together.

Dose Levels

Typically, a physician will determine the actual dosage which will be most suitable for an individual subject. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, and the individual undergoing treatment.

Depending upon the need, the agent may be administered at a dose of from 0.00001 ug/Kg body weight to 5 mg/Kg body weight, preferably 0.0001 µg/Kg to 5 mg/Kg, preferably 0.001 ug/Kg to 1 mg/Kg, preferably 0.01 ug/Kg to 500 ug/Kg, preferably 0.02 ug/Kg to 300 ug/Kg body weight. Preferably the composition comprises up to about 25 ug of each PorA/FetA component.

In a preferred embodiment, a dose of approximately 3 ug is administered to a child of approximately 3-4 Kg in weight.

Preferably compositions according to the present invention are essentially free from cellular components such as polysaccharide capsule material and/or vesicles.

Preferably the vaccine compositions according to the present invention are protein vaccine compositions.

Preferably the vaccine compositions of the present invention comprise an adjuvant. Any suitable adjuvant known in the art may be employed in the present invention. The person skilled in the art will vary the adjuvant and/or quantities or proportions thereof according to the immune response required. Preferably this adjuvant is Aluminium hydrogel.

Specific exemplary compositions are set out herein, in particular with reference to Table 3.

The invention will now be described by way of example with reference to the following figures:

EXAMPLE 1

Survey and Vaccine Compositions

Figure 1:
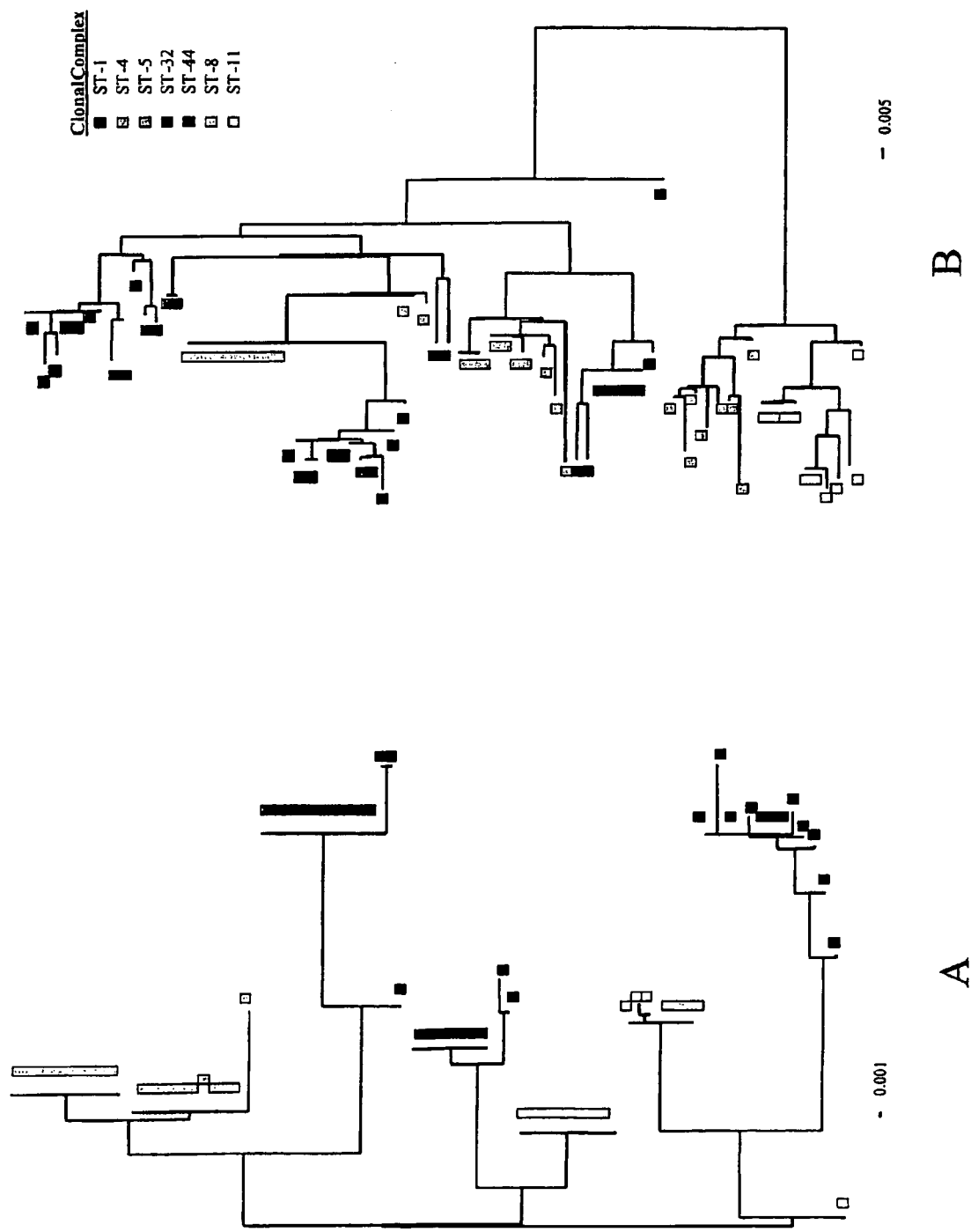
FIG. 1 shows phylogenetic analysis of 78 hyperinvasive meningococci using (A) 7 concatenated housekeeping gene sequences (3,284 base pairs) and (B) 3 concatenated antigen gene sequences (4,209 base pairs). Each isolate is colour coded according to clonal complex, as defined by Multilocus Sequence Typing (MLST).

This example presents vaccine compositions and methods for their production.

To inform the choice of variants to be included in meningococcal vaccines according to the present invention, a survey of the variation of three major OMPs, PorA, PorB, and FetA, was undertaken in a collection of 78 meningococci representing the seven hyper-invasive lineages associated with most meningococcal disease outbreaks of the latter half of the twentieth century. Surface protein sequences for the organism were provided. Analysis of the nucleotide sequences of the genes encoding these antigens revealed strong evidence for positive selection acting on those parts of the genes previously described as encoding immunogenic regions of all three proteins. Phylogenetic analysis of concatenated antigen gene sequences generated clusters that were congruent with clonal complex, although this congruence was less apparent when individual loci were analysed. Further, there was evidence for both the persistence of particular combinations of antigen variants during decades of global spread and the presence of identical antigen combinations in otherwise unrelated isolates. This antigenic structuring greatly simplified the number of components required for a vaccine that potentially provided cross-protection against all seven hyper-invasive lineages. For example, a vaccine according to the invention containing only six PorA combined with five FetA variants provides protection against all of the 78 isolates included in this study (see below).

Materials and Methods

Growth of meningococi and DNA preparation. A total of 78 meningococcal isolates, representative of the major meningococcal disease outbreaks reported in the latter half of the twentieth century were chosen for this analysis (Table 1). These isolates were previously characterised by multi-locus sequence typing (MLST), and included: 37 serogroup A meningococci (14 ST-1 complex, 11 ST-4 complex, 12 ST-5 complex); 10 isolates from ST-11 complex (8 serogroup C and 2 serogroup B); 8 isolates from ST-8 complex (5 serogroup B and 3 serogroup C); 10 ST-32 complex organisms (9 serogroup B, 1 serogroup C); 13 isolates from ST-41/44 complex (all serogroup B). Isolates were propagated on heated blood agar plates in an atmosphere of 5% $CO_2$ for 8-16 hours. Approximately $10^7$-$10^9$ colony forming units were used to prepare genomic DNA using an 'Isoquick Nucleic Acid Extraction Kit' (Orca Research Inc.), according to the manufacturer's protocol.

Nucleotide sequence determination and gene nomenclature. PCR amplification and nucleotide sequence determination of the meningococcal porA, porB, and fetA genes was as described previously (Suker, 1994 Mol. Micro. Vol 12 p. 253; Urwin, 1998 Epid. and Inf. Vol 121 p. 95; Thompson, 2003 Microbiology Vol 149 p. 1849). Nucleotide sequence data for forward and reverse strands were assembled with the STA-DEN software package, reformatted into 'GCG' format and aligned to maintain maximum positional homology using the SEQLAB program within the GCG software package Version 10.1 (Genetics Computer Group, Madison, Wis.). Using the Molecular Evolutionary Genetics Analysis (MEGA) software package version 2.0, pairwise comparisons were performed on each set of aligned sequences to identify distinct alleles; allele numbers were then assigned to each unique porA, porB, and fetA gene sequence on the basis of previously defined nomenclature systems (Thompson, 2003 ibid).

Variable region (VR) identification. The identification of the VRs of PorA and FetA was straightforward: nucleotide sequences encoding the defined PorA variable epitopes, VR1 and VR2, were translated and identified by querying the PorA VR sequence database located at http://neisseria.org/nm/typing/pora/. The amino acid sequence variants determined for the FetA VR were also identified by database interrogation at http://neisseria.org/nm/typing/feta/.

PorB VR identification was more complicated, as PorB proteins often have discontinuous epitopes, where several of the eight PorB surface-exposed variable loops are involved in epitope formation. As only loops II and III are essentially invariant in PorB, it was necessary to identify amino acid sequence variation in loops I, IV-VIII when determining PorB epitope diversity. Variation in PorB was therefore determined by pairwise comparisons of the aligned amino sequences corresponding to each surface loop, with reference to a previously published scheme (Sacchi, 1998 Clinical and Diagnostic Lab. Imm. Vol 5 p. 348). The results were reported using a scheme slightly modified from that of Poolman et al. (Frasch, 1985 Reviews of Infectious Diseases Vol. 7 p. 504), with the format serogroup:serotype:subtype:FetA type, thus: A:4,21:P1.5-2,10:F5-1. Thus the antigenically variable proteins were selected.

Data manipulation and analysis. Phylogenetic trees were constructed using the maximum likelihood (ML) method available in the PAUP* package. The GTR model of nucleotide substitution was used, with values for the nucleotide substitution matrix, the proportion of invariant sites, and the shape parameter (+) of a gamma distribution of rate variation among sites (with 4 categories) estimated during tree reconstruction. ML phylogenies were constructed using concatenated DNA sequences for (i) the 7 housekeeping gene fragments employed in MLST, giving a total sequence length of 3,284 bp and (ii) the three antigen gene sequences giving a total length of 4,209 base pairs.

Results

The incidence of each of the antigenically variable proteins in clinical occurrences was determined as follows.

Diversity of OMP genes and proteins. The lengths of the nucleotide sequences when aligned for analysis were: fetA, 2031 bp; porA, 1155 bp; and porB, 1023 bp. Similar levels of sequence diversity were observed at the three loci (Table 2) with 33 porA alleles encoding 33 PorA sequences, 33 fetA genes encoding 31 FetA sequences, and 31 porB alleles encoding 28 PorB sequences. Two distinct allele classes were present at the porB locus, porB2 and porB3, and the majority of differences among porB alleles were due to difference between these classes; there was less diversity within porB2 and porB3 alleles and their encoded proteins when analysed separately. Peptide sequence variation was identified in regions of the proteins implicated in immune responses in animals and man. At the FetA VR, 16 unique peptide sequences were identified. There were 12 PorA VR1 and 18 PorA VR2 peptides sequences (26 unique VR1, VR2 combinations), and 20 unique combinations of the peptide sequences corresponding to loops I, IV-VIII of the PorB protein (Table 1, Table 2).

Comparison of phylogenies obtained from antigen genes and housekeeping genes. A ML tree constructed with concatenated housekeeping genes clustered the isolates into their clonal complexes (FIG. 1A) with the exception of the ST-8 complex isolate B6116/77 which possessed a pdhC allele that was divergent from those present among other ST-8 isolates. Similar clusters of isolates were observed in the ML tree constructed from the concatenated sequences of the three antigen genes, although the deeper branching patterns of the two trees were different (FIG. 1B). The isolates belonging to the ST-1, ST-4, and ST-5 complexes, which were mostly serogroup A, formed a clade in the housekeeping gene tree but not in the antigen gene tree. Conversely, the isolates belonging to the ST-8 and ST-11 complexes formed a clade in the antigen gene tree, as a result of these isolates possessing porB alleles belonging to the porB2 allele class, whilst the remaining isolates possessed porB alleles of the porB3 class. The clade comprising isolates of the ST-4 complex and ST-41/44 complex in the antigen gene tree was a consequence of isolates sharing closely related fetA and porA genes. The clustering of two ST-32 complex isolates (204/92 and BZ83) with ST-1 isolates reflected identity or similarity of fetA, porA and porB alleles with ST-1 complex organisms. The oldest isolate in the collection (A4/M1027, ST-4) isolated in 1937 in the USA fell outside the otherwise closely related cluster of sequences formed by ST-4 complex meningococci because it had a porA-16 allele at the porA locus (Table 1), an allele predominant among ST-1 complex organisms. Three ST-1 complex meningococci did not cluster with the other ST-1 isolates due to fetA sequence diversity, isolates 20 and 254 having a fetA-8 allele and isolate 129 a fetA-57 allele, rather than the fetA-3 allele observed in most ST-1 complex isolates. Two ST-41/44 complex isolates (NG E30 and NG H36) did not cluster with the remaining isolates belonging to this complex as a result of divergent fetA and porA alleles.

Distribution of FetA and PorA antigenic variants among clonal complexes. There was similarity in patterns of variation identified in FetA and PorA protein sequences. Most variation was restricted to surface exposed loops 1 and 4 in PorA, corresponding to VR1 and VR2, and was found mainly in one surface exposed loop in FetA, corresponding to the FetA VR. Furthermore, variants of the major immunogenic regions of both FetA and PorA proteins were unevenly distributed among clonal complexes, with particular combinations of the three antigenic regions associated with individual clonal complexes (Table 1). The most common combination among the ST-1 complex isolates was P1.5-2,10;F5-1 (6/10 isolates) while ST-4 complex isolates were predominantly (6/10) P1.7,13-1:F1-5 and ST-5 complex isolates were predominantly (9/12) P1.20,9:F3-1. The majority (9/13) of ST-41/44 isolates were P1.7-2,4:F1-5. The ST-8 complex isolates analysed here contained a number of variants with no predominant VR sequences, although there was a predominance of the P1.5 VR1 sequence and its variants P1.5-1 and P1.5-2, the VR2 P1.2 and its P1.2-2 variant and the FetA VR F3-9. In some cases, e.g. isolates 255 (ST-4 complex), S4355 (ST-5 complex) and 400 (ST-41/44 complex), departure from the commonest combination was at a single variable region; in other cases, multiple differences were present. Among ST-11 complex isolates, for example, were two combinations with distinct peptide sequences: four isolates were P1.5,2: F1-1 and three P1.5,2-1:F5-5. Variants of the P1.7,16:F3-3 combination dominated the ST-32 complex organisms. In two cases, isolates with unrelated STs exhibited identical PorA and FetA types: the ST-41/44 complex isolate NG E30 was identical to ST-8 complex isolate BZ163, both being P1.21, 16:F1-7, although these isolates did not share identical porA and fetA alleles. One of the ST-32 isolates was identical to the majority antigenic type exhibited by ST-1 complex organisms, P1.5-2,10:F5-1 although again the allele sequences were not identical.

Distribution of PorB antigenic variants among clonal complexes. Amino acid variation was identified in all surface exposed loops of PorB except loops II and III. Conservation of PorB sequences was observed in all clonal complexes; extensive evidence of mosaic gene structure indicated that it was likely that most of this diversity had arisen by reassortment of known sequences. The majority of ST-1 complex organisms (11/14) possessed PorB3 proteins that were identical in all surface loops and were phenotypically identified as serotype 4,21. The PorB3 proteins of isolates 393 and 322/85 differed from the serotype 4,21 sequence only in variable loop I, while isolate 79126 expressed a serotype 4 PorB3 protein which was divergent in variable loops I, VI-III. All ST-4 complex meningococci possessed serotype 4,21 PorB proteins, although minor variation in surface loop VIII was identified in one isolate (2059001). The serotype 4,21 PorB3 protein identified among ST-4 complex organisms was distinguished from that identified in ST-1 complex and ST-5 complex meningococci by two amino acid changes in variable loop IV. Seven of ten ST-5 complex isolates had serotype 4,21 PorB3 proteins identical to those seen among ST-1 complex, while the remaining three isolates (92001, 11-004 and 80049) had one or two variant loop sequences in PorB3. Most ST-8 complex isolates (5/8) had identical serotype 2b PorB2 amino acid sequences, with amino acid changes observed in either loop IV or loop VIII of the remaining three isolates, 94/155, BZ10 and AK22 (BZ10 still reacted with the serotype 2b monoclonal antibody despite this variation). The PorB protein was well conserved among ST-11 complex meningococci: nine often isolates possessed identical PorB2 variable loops and corresponded to serotype 2a; isolate 90/18311 had variant amino acid sequences in loops V-VII and was not serotypable. Seven of ten ST-32 complex isolates examined had identical PorB3 proteins corresponding to serotype 15, while divergent sequences associated with reactivity with serotype 4 mAbs were identified in isolates 204/92 and BZ83. The remaining isolate (BZ169) possessed a PorB3 amino acid sequence identical to a serotype 1 reference strain. Among ST-41/44 complex organisms, four isolates shared identical PorB3 amino acid sequences corresponding to serotype 4. Three isolates (88/03415, NG E30, AK50) had variant PorB sequences, but were still defined as serotype 4 as they possessed the loop VI amino acid sequence recognised by serotype 4 monoclonal antibodies. Three isolates (NG H15, NG H36, N31905) had variant PorB3 sequences corresponding to serotype 8, while the remaining three ST-41/44 complex organisms possessed variant PorB3 proteins composed of novel combinations of variable loop sequences that were not typable by serological methods.

Temporal and geographic distribution of antigen gene variants and combinations. A number of antigen gene alleles exhibited wide temporal and geographical distributions. The porA-16 allele was identified in 16 meningococci isolated in 15 countries from five continents over a period of 55 years; porB3-26 was identified in 10 isolates obtained from 9 countries including India, the USA, and several African countries over a period of 53 years. The most widely distributed fetA allele in this collection was fetA-5 which was present in 11 isolates originating from 9 countries, mainly from Africa but including China and India, over 27 years. A number of sequences encoding the immunogenic variable regions of these proteins also exhibited longevity and global distribution; the FetA VR variant F1-5 was present in 26 members of the isolate collection including the oldest (A4/M1027, isolated in the USA in 1937) and the most recent isolate examined, (N45/96, isolated in Norway in 1996) (Table 1).

Discussion

The present analysis has, for the first time, assessed the allele diversity present at three distinct OMP-encoding loci in the major hyper-invasive meningococcal lineages. The results confirmed the extensive diversity of these proteins, with between 28 and 33 peptide sequences observed for each protein and provided evidence for the structuring of combinations of these variants.

Although recombination has erased most of the deeper phylogenetic signal in meningococcal populations, groups of related genotypes, likely to comprise meningococci that share a common ancestor, can be identified by a number of means. MLST resolves these related genotypes as clonal complexes, which are defined by allelic differences rather than nucleotide sequence comparisons per se, to account for frequent recombination. The ML trees for both housekeeping gene sequences and antigen gene sequences generated clades that were largely congruent with clonal complex for the representatives of the seven hyper-invasive lineages analysed here. While congruence of phylogenies based on housekeeping genes with clonal complex designation was unremarkable, the distribution of antigen gene sequences illustrated in the phylogenetic analysis was unexpected.

Strictly clonal processes cannot account for congruence of the combinations of antigen variants with clonal complex as the meningococcus experiences frequent recombination. The predictions of clonality are further violated by the presence of identical antigen gene sequences throughout the data set, regardless of clonal complex. The 'epidemic clone' concept, in which non-clonal populations can be transiently dominated by particular genotypes that share a recent common ancestor, could be invoked to explain the observations. However, this would not explain the longevity of antigen combinations over decades of global spread nor the two examples of the presence of identical antigen variant combinations in otherwise genetically unrelated isolates.

The 'epidemic clone' population structure also provides no explanation for the non-overlapping nature of the antigen combinations observed In the majority of cases, the clonal complexes representative of particular hyper-invasive lineages have predominant antigen gene combinations that share no major antigen variants with other clonal complexes. There were some examples of sharing identical antigen variants among combinations, for example, the ST-4 complex shared the P1.7 variant with ST-32 complex and the F1-5 variant with ST-41/44 complex; however, neither of the latter clonal complexes have been recently reported in Africa, where all of the recent ST-4 isolates originated, therefore it is possible that these overlapping antigen variant complexes are not present simultaneously in the same transmission system. By contrast, although possibly related by descent, all of the serogroup A-associated clonal complexes that have recently caused disease in Africa (ST-1, ST-4 and ST-5) have distinct, non-overlapping antigen gene combinations.

Models of strain structuring on the basis of host immunity provide a theoretical framework that can accommodate the observed combinations of antigenic variants. These models postulate that, within a given transmission system, pathogen strains that share immunological variants are disadvantaged. In this respect, it was noteworthy that a number of clonal complexes contained antigenic variant combinations that were altered at multiple antigens. There was evidence for two globally-circulating strains within the ST-11 complex, P1.5, 2:F1-1 and P1.5,2-1:F5-5 and one of these variants was associated with two different capsules, with two isolates that were B:2a:P1.5,2:F1-1 and two C:2a:P1.5,2:F1-1. At least two ST-32 complex variants spread widely from the mid-1970s onwards and these also displayed non-overlapping combinations of OMP antigen variants. The 'Norwegian' strain was typically B:15:P1.7,16;F3-3 while the 'Spanish' strain was B:4:P1.19,15;F5-1. A further variant identified in the Netherlands and the UK was notable for being identical at the level of OMPs (4:P1.5-2,10:F5-1) with many ST-1 complex isolates. A final variant identified in Chile, whilst bearing some similarities with the Norwegian strain, also differed at many OMPs being B:15:P1.7,3:F3-1. Many examples of these strains within the ST-32 complex have been described previously by serological and molecular technique. Many of the exceptions to the non-overlapping structure involved PorB and PorA VR1; there is some evidence that these antigens may be relatively less immunogenic than PorA VR2. In conclusion, it is possible that meningococcal strains or transmission variants may, at least in part, be defined by OMP variant combinations, especially those of FetA VR and PorA VR2. Thus, a sub-group of antigens was selected from the antigenically variable proteins found in clinical occurrences. This selection is extended to the epitope level as explained.

Whatever the mechanism by which meningococcal antigen variants are structured, the present invention makes use of the observed structuring in novel vaccine design.

The results of this survey are consistent with a limited repertoire of antigen variant combinations dominating the major meningococcal hyper-invasive lineages. The non-overlapping nature of the combinations observed was consistent with strain structure imposed by herd immunity. If this is the case, some low frequency variants in the population may have a short term selective advantage within a single host, but there is some evidence that such variants are likely to be less fit during epidemic spread. This framework further predicts that novel variants can emerge and spread from time to time if they are distinct at multiple loci encoding immunodominant antigen variants, and that distinct genotypes can possess identical antigen types; both of these phenomena are present in this data set. Moreover, as bacteria are less likely to change, by mutation or recombination, at two distantly located genes simultaneously, a vaccine that targets at least two distinct variable antigens will exhibit improved efficacy over a vaccine with multiple variants of a single antigen.

The isolates employed in this analysis represent the major hyper-invasive lineages reported over the last 60 years. Thus the invention provides relatively simple meningococcal OMP-based vaccines effective against all hyper-invasive lineages, regardless of serogroup.

Indeed, the survey showed that as few as 6 PorA variants (P1.5-1,2-2, P1.5-2,16, P1.5,10, P1.7,13-1, P1.7-2,4, P120,9) combined with 5 FetA variants (F1-5, F3-1, F5-1, F3-9, F5-5) provides homologous protection against all 78 isolates. This combination of PorA and FetA antigens according to the present invention variants protects against 95 of the 107 (89%) diverse meningococcal isolates used to develop MLST from which the 78 representative of the hyper-invasive lineages were derived. Thus the invention provides a vaccine composition comprising 11 different antigens, wherein said 11 antigens comprise six PorA antigens and five FetA antigens. In more detail, the invention provides a vaccine composition comprising 6 PorA variants (P1.5-1,2-2, P1.5-2,16, P1.5,10, P1.7,13-1, P1.7-2,4, P120,9) combined with 5 FetA variants (F1-5, F3-1, F5-1, F3-9, F5-5).

TABLE 1

The porA, fetA and porB allele sequences of 78 hyper-invasive meningococci.

| Clonal complex | Isolate | Year | Country | Serogroup | ST | Allele porA | fetA | porB | Epitope[a] PorA_VR1 | PorA_VR2 | FetA_VR | Serotype[b] (PorB) |
|---|---|---|---|---|---|---|---|---|---|---|---|---|
| ST-1 complex/ | 6748 | 1971 | Canada | A | 1 | 17 | 3 | 3-60 | 18-1 | 3 | F5-1 | 4, 21 |
| subgroup I/II | 20 | 1963 | Niger | A | 1 | 16 | 8 | 3-60 | 5-2 | 10 | F1-7 | 4, 21 |
| | 254 | 1966 | Djibouti | A | 1 | 16 | 8 | 3-60 | 5-2 | 10 | F1-7 | 4, 21 |
| | 129 | 1964 | West Germany | A | 1 | 16 | 57 | 3-60 | 5-2 | 10 | F3-6 | 4, 21 |
| | 371 | 1980 | India | A | 1 | 16 | 30 | 3-60 | 5-2 | 10 | F5-1 | 4, 21 |
| | 139M | 1968 | Philippines | A | 1 | 16 | 3 | 3-60 | 5-2 | 10 | F5-1 | —[c] |
| | 120M | 1967 | Pakistan | A | 1 | 16 | 56 | 3-60 | 5-2 | 10 | F5-1 | 4, 21 |
| | S5611 | 1977 | Australia | A | 1 | 16 | 3 | 3-60 | 5-2 | 10 | F5-1 | — |
| | 106 | 1967 | Morocco | A | 1 | 16 | 3 | 3-60 | 5-2 | 10 | F5-1 | 4, 21 |
| | 393 | 1968 | Greece | A | 1 | 16 | 3 | 3-59 | 5-2 | 10 | F5-1 | — |
| | 322/85 | 1985 | East Germany | A | 2 | 16 | 52 | 3-80 | 5-2 | 10 | F5-2 | 4, 21 |
| | 79128 | 1979 | China | A | 3 | 54 | 10 | 3-60 | 7-1 | 10 | F5-5 | — |
| | BZ 133 | 1977 | Netherlands | B | 1 | 2 | 3 | 3-60 | 7 | 16 | F5-1 | NT[d] |
| | 79126 | 1979 | China | A | 3 | 22 | 10 | 3-01 | 7-3 | 10-5 | F5-5 | 4 |
| ST-4 complex/ | A4/M1027 | 1937 | USA | A | 4 | 16 | 45 | 3-26 | 5-2 | 10 | F1-5 | 4, 21 |
| subgroup IV | 26 | 1963 | Niger | A | 4 | 45 | 5 | 3-26 | 7 | 13 | F1-5 | — |
| | 243 | 1966 | Cameroon | A | 4 | 45 | 5 | 3-26 | 7 | 13 | F1-5 | — |
| | 2059001 | 1990 | Mali | A | 4 | 45 | 5 | 3-46 | 7 | 13 | F1-5 | 4, 21 |
| | 10 | 1963 | Burkina Faso | A | 4 | 21 | 5 | 3-26 | 7 | 13-1 | F1-5 | — |
| | 255 | 1966 | Burkina Faso | A | 4 | 24 | 5 | 3-26 | 7-5 | 13-1 | F1-5 | 4, 21 |
| | S3131 | 1973 | Ghana | A | 4 | 21 | 5 | 3-26 | 7 | 13-1 | F1-5 | — |
| | 690 | 1980 | India | A | 4 | 21 | 5 | 3-26 | 7 | 13-1 | F1-5 | 4, 21 |
| | C751 | 1983 | Gambia | A | 4 | 21 | 5 | 3-26 | 7 | 13-1 | F1-5 | — |
| | 1014 | 1985 | Sudan | A | 4 | 21 | 5 | 3-26 | 7 | 13-1 | F1-5 | — |
| | D8 | 1990 | Mali | A | 4 | 21 | 5 | 3-26 | 7 | 13-1 | F1-5 | — |
| ST-5 complex/ | IAL2229 | 1976 | Brazil | A | 5 | 19 | 55 | 3-27 | 20 | 9 | F2-1 | — |
| subgroup III | 153 | 1966 | China | A | 5 | 19 | 7 | 3-47 | 20 | 9 | F3-1 | 4, 21 |
| | 154 | 1966 | China | A | 6 | 19 | 7 | 3-47 | 20 | 9 | F3-1 | 4, 21 |
| | 14/1455 | 1970 | USSR | A | 5 | 19 | 7 | 3-47 | 20 | 9 | F3-1 | 4, 21 |
| | S4355 | 1974 | Denmark | A | 5 | 20 | 7 | 3-27 | 5-1 | 9 | F3-1 | 4, 21 |
| | 7891 | 1975 | Finland | A | 5 | 19 | 7 | 3-27 | 20 | 9 | F3-1 | 4, 21 |
| | F4698 | 1987 | Saudi | A | 5 | 19 | 11 | 3-47 | 20 | 9 | F3-1 | — |
| | H1964 | 1987 | UK | A | 5 | 19 | 11 | 3-47 | 20 | 9 | F3-1 | — |

TABLE 1-continued

The porA, fetA and porB allele sequences of 78 hyper-invasive meningococci.

| Clonal complex | Isolate | Year | Country | Serogroup | ST | Allele porA | Allele fetA | Allele porB | Epitope[a] PorA_VR1 | Epitope[a] PorA_VR2 | Epitope[a] FetA_VR | Serotype[b] (PorB) |
|---|---|---|---|---|---|---|---|---|---|---|---|---|
| | F6124 | 1988 | Chad | A | 5 | 19 | 11 | 3-47 | 20 | 9 | F3-1 | — |
| | 92001 | 1992 | China | A | 7 | 19 | 7 | 3-62 | 20 | 9 | F3-1 | — |
| | 11-004 | 1984 | China | A | 5 | 19 | 54 | 3-61 | 20 | 9 | F3-8 | — |
| | 80049 | 1963 | China | A | 5 | 16 | 5 | 3-56 | 5-2 | 10 | F1-5 | 4 |
| ST-8 complex/ | BZ 10 | 1967 | Netherlands | B | 8 | 7 | 4 | 2-20 | 5-1 | 2-2 | F3-9 | 2b |
| cluster A4 | B6116/77 | 1977 | Iceland | B | 10 | 7 | 17 | 2-03 | 5-1 | 2-2 | F1-4 | — |
| | BZ 163 | 1979 | Netherlands | B | 9 | 1 | 38 | 2-03 | 21 | 16 | F1-7 | 2b |
| | G2136 | 1986 | England | B | 8 | 46 | 20 | 2-03 | 5-2 | 10-1 | F3-6 | — |
| | SB25 | 1990 | South Africa | C | 8 | 51 | 4 | 2-03 | 18-1 | 3 | F3-9 | — |
| | AK22 | 1992 | Greece | B | 8 | 16 | 4 | 2-30 | 5-2 | 10 | F3-9 | — |
| | 94/155 | 1994 | New Zealand | C | 66 | 9 | 4 | 2-21 | 5 | 2 | F3-9 | — |
| | 312901 | 1996 | England | C | 8 | 9 | 18 | 2-03 | 5 | 2 | F1-7 | — |
| ST-11 complex/ | 38VI | 1964 | USA | B | 11 | 9 | 47 | 2-02 | 5 | 2 | F1-1 | — |
| ET-37 complex | NG P20 | 1969 | Norway | B | 11 | 9 | 9 | 2-19 | 5 | 2 | F1-1 | 2a |
| | F1576 | 1984 | Ghana | C | 11 | 9 | 9 | 2-47 | 5 | 2 | F1-1 | 2a |
| | 500 | 1984 | Italy | C | 11 | 9 | 9 | 2-02 | 5 | 2 | F1-1 | 2a |
| | MA-5756 | 1985 | Spain | C | 11 | 27 | 6 | 2-02 | 5 | 2-1 | F5-5 | 2a |
| | M597 | 1988 | Israel | C | 11 | 27 | 6 | 2-02 | 5 | 2-1 | F5-5 | 2a |
| | D1 | 1989 | Mali | C | 11 | 27 | 37 | 2-02 | 5 | 2-1 | F5-4 | 2a |
| | 90/18311 | 1990 | Scotland | C | 11 | 27 | 6 | 2-31 | 5 | 2-1 | F5-5 | NT |
| | L93/4286 | 1993 | England | C | 11 | 67 | 27 | 2-02 | 5-1 | 10-4 | F3-6 | — |
| | BRAZ10 | 1976 | Brazil | C | 11 | 70 | 36 | 2-02 | 5-1 | 10-1 | F1-10 | 2a |
| ST-32 complex/ | 8680 | 1984 | Chile | B | 32 | 41 | 15 | 3-24 | 7-2 | 3 | F3-1 | 15 |
| ET-5 complex | BZ 83 | 1984 | Netherlands | B | 34 | 16 | 53 | 3-01 | 5-2 | 10 | F5-1 | NT |
| | 204/92 | 1992 | Cuba | B | 33 | 4 | 26 | 3-08 | 19 | 15 | F5-1 | — |
| | EG 329 | 1985 | East Germany | B | 32 | 60 | 49 | 3-24 | 7-1 | 16 | F1-2 | 15 |
| | NG 080 | 1981 | Norway | B | 32 | 2 | 1 | 3-24 | 7 | 16 | F3-3 | 15 |
| | BZ 169 | 1985 | Netherlands | B | 32 | 14 | 1 | 3-14 | 5-2 | 16 | F3-3 | NT |
| | 44/76 | 1976 | Norway | B | 32 | 2 | 1 | 3-24 | 7 | 16 | F3-3 | — |
| | NG144/82 | 1982 | Norway | B | 32 | 2 | 1 | 3-63 | 7 | 16 | F3-3 | 15 |
| | 196/87 | 1987 | Norway | C | 32 | 61 | 1 | 3-24 | 7-2 | 16-12 | F3-3 | 15 |
| | NG PB24 | 1985 | Norway | B | 32 | 57 | 1 | 3-24 | 7-2 | 16-7 | F3-3 | NT |
| ST-41/44 | 931905 | 1993 | Netherlands | B | 41 | 39 | 2 | 3-16 | 7-2 | 4 | F1-5 | — |
| complex/ | 50/94 | 1994 | Norway | B | 45 | 39 | 2 | 3-51 | 7-2 | 4 | F1-5 | — |
| Lineage 3 | 88/03415 | 1988 | Scotland | B | 46 | 39 | 2 | 3-49 | 7-2 | 4 | F1-5 | — |
| | 91/40 | 1991 | New Zealand | B | 42 | 39 | 2 | 3-01 | 7-2 | 4 | F1-5 | 4 |
| | AK50 | 1992 | Greece | B | 41 | 39 | 16 | 3-52 | 7-2 | 4 | F1-5 | — |
| | BZ198 | 1986 | Netherlands | B | 41 | 39 | 2 | 3-01 | 7-2 | 4 | F1-5 | NT |
| | M-101/93 | 1993 | Iceland | B | 41 | 39 | 2 | 3-01 | 7-2 | 4 | F1-5 | — |
| | M40/94 | 1994 | Chile | B | 41 | 39 | 2 | 3-53 | 7-2 | 4 | F1-5 | — |
| | N45/96 | 1996 | Norway | B | 41 | 39 | 16 | 3-01 | 7-2 | 4 | F1-5 | — |
| | 400 | 1991 | Austria | B | 40 | 52 | 2 | 3-36 | 7-2 | 13-2 | F1-5 | — |
| | NG E30 | 1988 | Norway | B | 44 | 1 | 46 | 3-45 | 21 | 16 | F1-7 | 4 |
| | NG H15 | 1988 | Norway | B | 43 | 65 | 2 | 3-54 | 19 | 15-2 | F1-5 | 8 |
| | NG H36 | 1988 | Norway | B | 47 | 18 | 41 | 3-16 | 5-1 | 2-2 | F1-7 | 8 |

[a]PorA epitopes VR1 and VR2 together with the FetA VR were determined by translation of nucleotide sequences followed by database interrogation.
[b]The serotype of the PorB protein is stated, where available.
[c]—, serotype not available.
[d]NT: not typable.

TABLE 2

Genetic and antigenic diversity among 78 hyper-invasive meningococci.

| Locus | Nucleotide sequence length (bp) | Number of alleles | Proportion of segregating sites | Mean p-distance | Number of peptide sequences | Number of VR combinations[a] |
|---|---|---|---|---|---|---|
| porA | 1086-1149 | 33 | 0.14 | 0.041 | 33 | 26 |
| fetA | 1977-2019 | 33 | 0.19 | 0.051 | 31 | 16 |
| porB[b] | 927-1020 | 31 | 0.36 | 0.131 | 28 | 26 |
| porB2 | 1020 | 8 | 0.05 | 0.016 | 8 | 6 |
| porB3 | 927-939 | 23 | 0.10 | 0.031 | 20 | 2 |

[a]porA, VR1 and VR2 combinations; fetA, VR sequences, porB, variable loops I, IV-VIII combinations.
[b]Divergent, alternate alleles (porB2 and porB3) are present at the meningococcal porB locus.

EXAMPLE 2

Vaccine Compositions

Composition of Meningococcal PorA/FetA Vaccines

The analysis and methodology presented in Example 1 allows design of particular vaccine compositions according to the present invention.

Table 3 shows seven protein-based anti-meningococcal vaccine compositions that contain different combinations of the purified PorA and FetA proteins according to the present invention.

These 'recipes' are advantageously consistent with currently available epidemiological information.

The number of proteins required in each vaccine is given, together with the particular epitopes included and together with the coverage attained for a number of different scenarios.

The vaccine coverage has been calculated for a number of isolate collections as the percentage of isolates with at least one epitope homologous to a vaccine epitope. The collection of 107 isolates was assembled in 1996 to be representative of global disease in the latter half of the twentieth century. The meningococci belonging to the UK isolate collections from 1975-1995 are representative of the disease-associated isolates obtained in the UK over this period.

The African/Asian vaccine particularly high coverage given the relatively limited diversity of disease-causing meningococci in these areas.

For comparitive purposes, the coverage of each of these isolate collections that is attained by the prior art meningococcal serogroup C Conjugate (MCC) vaccine, introduced on a population scale in 1999, is given as a comparison. It is noteworthy that this vaccine, currently in routine use, is only approximately one-third to one-half as effective as each of the three clonal complex directed PorA/FetA vaccine compositions according to the present invention (ST-11, ST-32 and ST-41/44). Furthermore, it is only one-sixth to one-ninth as effective as the standard/enhanced and geographically directed vaccine compostions according to the present invention (see first four rows of Table 3), based on the percentage coverage of the global collection of 107 disease-causing isolates. Thus the compositions of the present invention are extremely effective and considerably better than prior art compositions such as the MCC vaccine.

A summary of the compositions given in table 3 is presented below:

Standard
P1.5-1 P1.2-2 F1-5 P1.5-2 P1.16 F3-1 P1.5 P1.10 F5-1 P1.7 P1.13-1 F3-9 P1.7-2 P1.4 F5-5 P1-20 P1.9
Enhanced
P1.5-1 P1.2-2 F1-5 P1.5-2 P1.16 F3-1 P1.5 P1.10 F5-1 P1.7 P1.13-1 F3-9 P1.7-2 P1.4 F5-5 P1-20 P1.9 P1.19 P1.15
Europe/USA
P1.5-1 P1.2-2 F1-5 P1.5-2 P1.16 F3-6 P1.5 P1.10 F5-1 P1.7 P1.4 F4-1 P1.7-2 P1.2 F3-9 P1.19 P1.15 F1-7
Africa/Asia
P1.5-2 P1.10 F5-1 P1.7 P1.13-1 F1-5 P1-20 P1.9 F3-1
ST-11 Complex
P1.5 P1.2 F3-6 F5-1
ST-32 Complex
P1.7 P1.16 F3-1 P1.19 P1.15
ST-41/44 Complex
P1.7-2 P1.4 F1-5 F1-7

TABLE 3

Table: Recipes for PorA/FetA meningococcal vaccines.

| | Epitope composition | | | Number | % coverage of isolate collection | | | | |
| --- | --- | --- | --- | --- | --- | --- | --- | --- | --- |
| Vaccine | PorA VR1 | PorA VR2 | FetA | of proteins | 107 global | 1975 UK | 1985 UK | 1995 UK | 1975-1995 UK |
| Standard | P1.5-1 | P1.2-2 | F1-5 | 11 | 88.79 | 84.80 | 90.00 | 95.00 | 89.54 |
| | P1.5-2 | P1.16 | F3-1 | | | | | | |
| | P1.5 | P1.10 | F5-1 | | | | | | |
| | P1.7 | P1.13-1 | F3-9 | | | | | | |
| | P1.7-2 | P1.4 | F5-5 | | | | | | |
| | P1-20 | P1.9 | | | | | | | |
| Enhanced | P1.5-1 | P1.2-2 | F1-5 | 12 | 90.65 | 88.80 | 91.00 | 96.00 | 91.69 |
| | P1.5-2 | P1.16 | F3-1 | | | | | | |
| | P1.5 | P1.10 | F5-1 | | | | | | |
| | P1.7 | P1.13-1 | F3-9 | | | | | | |
| | P1.7-2 | P1.4 | F5-5 | | | | | | |
| | P1-20 | P1.9 | | | | | | | |
| | P1.19 | P1.15 | | | | | | | |
| Europe/ USA | P1.5-1 | P1.2-2 | F1-5 | 12 | 81.31 | 92.80 | 90.00 | 94.00 | 92.31 |
| | P1.5-2 | P1.16 | F3-6 | | | | | | |
| | P1.5 | P1.10 | F5-1 | | | | | | |
| | P1.7 | P1.4 | F4-1 | | | | | | |
| | P1.7-2 | P1.2 | F3-9 | | | | | | |
| | P1.19 | P1.15 | F1-7 | | | | | | |
| Africa/ Asia | P1.5-2 | P1.10 | F5-1 | 6 | 60.74 | 34.40 | 66.00 | 51.00 | 49.23 |
| | P1.7 | P1.13-1 | F1-5 | | | | | | |
| | P1-20 | P1.9 | F3-1 | | | | | | |
| ST-11 complex | P1.5 | P1.2 | F3-6 | 3 | 23.36 | 47.20 | 29.00 | 43.00 | 35.80 |
| | | | F5-1 | | | | | | |
| ST-32 complex | P1.7 | P1.16 | F3-1 | 3 | 30.84 | 12.80 | 42.00 | 17.00 | 23.08 |
| | P1.19 | P1.15 | | | | | | | |
| ST-41/44 complex | P1.7-2 | P1.4 | F1-5 | 3 | 32.71 | 24.80 | 33.00 | 42.00 | 32.62 |
| | | | F1-7 | | | | | | |
| MCC (for comparison) | N/A | N/A | N/A | N/A | 11.00 | 20.00 | 25.00 | 36.00 | 26.46 |

EXAMPLE 3

Cloning and Expression of PorA/FetA Epitopes

Expression vector pET30 EkLIC vector (Novagen) is used in conjunction with ligation-independent cloning (LIC), which advantageously requires no restriction digests or ligation. This example illustrates the potential for co-expression of multiple proteins.

The expression system chosen in this example has the features of being IPTG inducible from T7 lac promoter. The system incorporates a His-tag for column purification (majority of clones with N-terminal His-tag, some with C-terminal H is tag also). The system incorporates an enterokinase site for cleaving off N-terminal H is tag if necessary or desirable. The system advantageously produces inclusion bodies for ease of purification—PorA and FetA genes are cloned without signal sequence to allow their expression in inclusion bodies.

In this example, the pET 30 EkLIC vector is used with a cloning method comprising PCR-amplifying FetA and PorA genes with specific ends compatible with LIC cloning. These are then treated with T4 DNA polymerase and dATP to create 5' overhangs. The treated insert is then annealed to pre-linearised vector. The annealed constructs are then transformed into a cloning host leading to formation of circular plasmid. These plasmids are then screened by transforming into an expression host. Other methods such as sequencing, western blots (PorA MAbs, His-tag MAb) are employed to verify the clones as required.

PorA types cloned are shown in table A; *Strain 3072 from the enhanced combination, all other strains make up the standard combination.

FetA types cloned are shown in table B; All these types are for the standard vaccine combination

EXAMPLE 4

Production of PorA/FetA Protein Antigens

In this example, IPTG induction is used to trigger expression of cloned PorA/FetA protein antigens from example 3. BL21 (DE3) transformed with the PorA/PetA clones are grown on Luria agar/broth supplemented with 30 µg/ml Kanamycin. Basal expression is suppressed by inclusion of 1% glucose.

Protocol: Production

Starter culture—Inoculate 50 ml LB in universal with one colony BL21 (DE3) clone and grow overnight at 37° C. in shaking incubator. Measure OD600 and inoculate 500 ml LB to OD600=0.05. Incubate at 37° C. in shaking incubator, 250 rpm to OD600=0.5-0.6. Induce by adding IPTG to 1 mM final concentration. Return to shaking incubator for 2-3 hours. Transfer culture to centrifuge tubes. Incubate on ice for 5 mins. Harvest cells by centrifugation and freeze at −70° C.

Protocol: Inclusion Body Purification

Resuspend the cell pellet in BugBuster™ protein extraction reagent. Add Lysonase (Lysozyme and nuclease). Incubate on a shaking platform until no longer viscous. Spin 12.5 k rpm 20 min at 4° C. Resuspend the pellet in the same volume of BugBuster™ reagent. Add rLysozyme solution. Vortex and incubate at room temperature for 5 min. Add 6 vol 1:10 diluted BugBuster™ reagent. Spin 6.5 k rpm 15 min at 4° C. to collect the inclusion bodies.

Protocol: Further Protein Purification from Inclusion Bodies

Wash inclusion bodies with 0.5 vol of 1:10 diluted BugBuster™. Repeat wash, spin 12.5 k rpm for 15 min at 4° C.

and remove the supernatant. Denature pellet to 20 mg wet weight/ml in TE 8.0 M urea. Spin 12.5 k rpm, 10 mins. Make up Supernatant to 4.0 M urea, 0.5 M NaCl, 1% Z3-14. Refold by dialysing against 20 mM Tris HCl pH7.9, 250 mM NaCl, 0.05% Z3-14. Spin 10 K, 10 mins. Reserve the supernatant containing solubilised protein.

Following inclusion body purification, it is preferred to proceed with a tag (in this example 6his tag) based purification—in this example Nickel column purification is used.

Nickel Column Purification

His-bind Resin (Novagen) is used. Completely resuspend the resin. Transfer the slurry (2× column volume) to a column. Allow the resin to pack under gravity flow.

Charge and equilibrate the column by applying:

3 volumes sterile deionised water 5 volumes 1× Charge Buffer (Nickel sulphate)

3 volumes 1× Binding Buffer+0.05% Z3-14

Protocol: Column Chromatography

Filter protein sample through 0.45 um filter. Bind protein extract to column.

Wash with 10×vol. Binding Buffer+0.05% Z3-14 (20 mM Imidazole)

Wash with 6×vol. Wash Buffer+0.05% Z3-14 (60 mM Imidazole)

Elute with 6×vol. Elute Buffer+0.05% Z3-14 (1 M Imidazole)

Final buffer: Dialyse against 10 mM Tris HCl, 150 mM NaCl, 0.1% TritonX-100.

Figure 2:
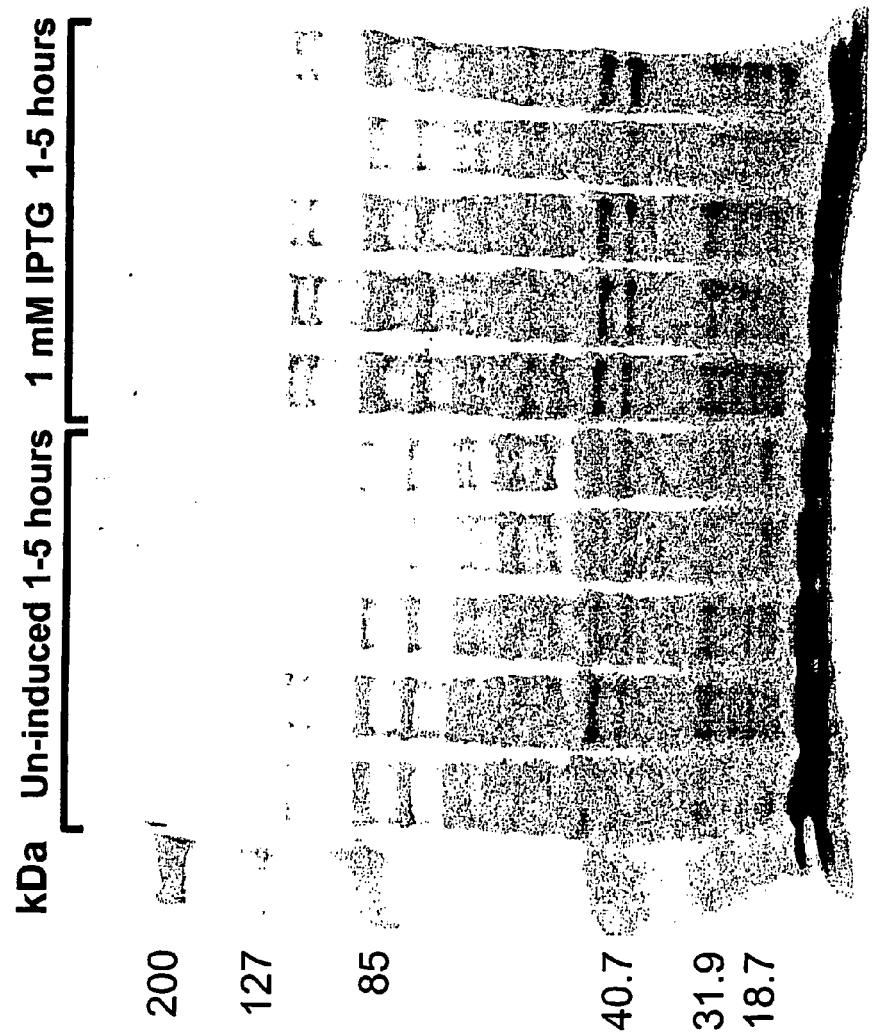
FIG. 2 shows coomassie stained PAGE protein samples.

In this example, PorA P1.7-2,4 are expressed. Referring to FIG. 2, lane 1 is molecular weight markers, numbers are in kDa; lanes 2-6 are un-induced 1-5 hours; lanes 7-11 are 1 mM IPTG treatment 1-5 hours.

Figure 3:
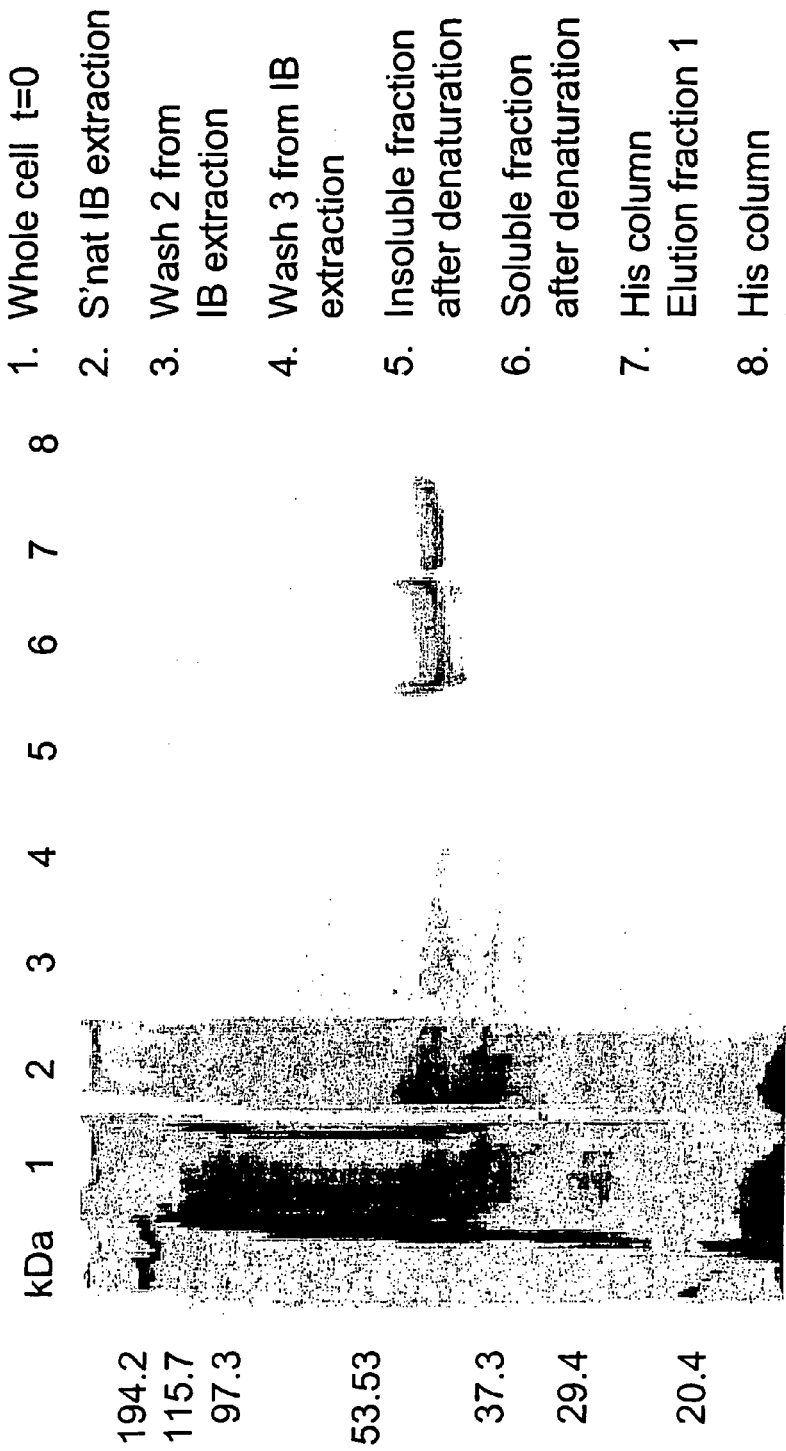
FIG. 3 shows PAGE protein samples from various different treatments/conditions (see examples for details).

Referring to FIG. 3, PorA P1.7-2,4 fractionation is shown. Lane 0 is molecular weight markers, numbers are in kDa; lane 1 is Whole cell t=0; lane 2 is supernatent IB extraction; lane 3 is Wash 2 from IB extraction; lane 4 is Wash 3 from IB extraction; lane 5 is Insoluble fraction after denaturation; lane 6 is Soluble fraction after denaturation; lane 7 is H is column Elution fraction 1; lane 8 is H is column Elution fraction 2.

According to this example, approx. 6 mg purified protein is produced from 500 ml culture after inclusion body (IB) extraction and His-bind (Nickel column) purification.

TABLE A

Por A Types cloned

| Strain for PorA | PorA | VR1 (MAb) | VR2 (MAb) |
|---|---|---|---|
| 2726 | P1.7- | PLPNIQPQVTKR (SEQ ID NO: 1) | YYTKDTNNNLTLV (SEQ ID NO: 10) |
| 2341 | P1.5, 10 | PLQNIQPQVTKR (SEQ ID NO: 2) | HFVQNKQNQRPTL (SEQ ID NO: 11) |
| 2763 | P1.7, 13- | AQAANGGASGQVKVT (SEQ ID NO: 3) | YWTTVNTGSATTT (SEQ ID NO: 12) |
| 2757 | P1.7-2, 4 | AQAANGGASGQVKVT (SEQ ID NO: 4) | HVVVNNKVATHVP (SEQ ID NO: 13) |
| 2760 | P1.20, 9 | QPQTANTQQGGKVKV (SEQ ID NO: 5) | YVDEQSKYHA (SEQ ID NO: 14) |

TABLE A-continued

Por A Types cloned

| Strain for PorA | PorA | VR1 (MAb) | VR2 (MAb) |
|---|---|---|---|
| 2794 | P1.5-1, 2- | PLQNIQQPQVTKR (SEQ ID NO: 6) | HFVQQTPQSQPTLV (SEQ ID NO: 15) |
| 3072* | P1.19, 15 | PPSKSQPQVKVTKA (SEQ ID NO: 7) | HYTRQNNADVFVP (SEQ ID NO: 16) |
| 2828 | P15-2, 10 | PLPNIQPQVTKR (SEQ ID NO: 8) | HFVQNKQNQRPTL (SEQ ID NO: 17) |
| 2740 | P1.5, 2 | PLQNIQPQVTKR (SEQ ID NO: 9) | HFVQQTPKSQPTLV (SEQ ID NO: 18) |

TABLE B

FetA types cloned

| Strain for FetA | fetA VR |  |
|---|---|---|
| 2757 | F1-5 | SQFKIEDKEKATDEEKNKNRENEKIAKAYRLT (SEQ ID NO: 19) |
| 2760 | F3-1 | GEFSIPTKEKKNGKEVDKPMEQQKKDRADEATVHAYKLS (SEEQ ID NO: 20) |
| 2769 | F5-1 | GEFEISGKKKDPKDPKKEIDKTDEEKAKDKKDMDLVHSYKLS (SEQ ID NO: 21) |
| 2758 | F3-9 | SKFSIPTTEKKNGQDVAKPADQQAKDRKDEALVHSYRLT (SEQ ID NO: 22) |
| 2786 | F5-5 | GKFKISDKKPDPNDPTKEIDKDAAEKAKDKKDMDLVHSYKLS (SEQ ID NO: 23) |

---

The invention claimed is:

1. An immunogenic composition comprising a purified PorA protein antigen and a purified FetA protein antigen in a suitable pharmaceutical carrier, wherein said PorA protein antigen is a PorA epitope selected from P1.5-1, P1.5-2, P1.5, P1.7, P1.7-2, P1.19, P1-20, P1.2-2, P1.2, P1.4, P1.9, P1.10, P1.13-1, P1.15 and P1.16 and wherein said FetA protein antigen is a FetA epitope selected from F1-5, F1-7, F3-1, F3-6, F3-9, F4-1, F5-1 and F5-5 and wherein said purified protein antigens are not present in outer membrane vesicles (OMVs).

2. An immunogenic composition comprising a combination of purified PorA and purified FetA epitopes each consisting of the amino acid sequence selected from SEQ ID NO:

1-23 and wherein said purified epitopes are not present in outer membrane vesicles (OMVs) in said composition.

3. The composition according to claim 1, wherein said composition comprises at least 1 PorA VR1 epitope and at least one PorA VR2 epitope.

4. The composition of claim 3, wherein the VR1 epitope comprises a the amino acid sequence selected from SEQ ID NO: 1-9 and the VR2 epitope comprises the amino acid sequence selected from SEQ ID NO: 10-18.

5. The composition according to claim 1, wherein said FetA epitope is F1-5, F3-1, F3-9, F5-1 or F5-5.

6. The composition according to claim 1, wherein said PorA epitope is P1.5-2, P1.10, P1.7 or P1.13-1 and said FetA epitope is F5-1 or F1-5.

7. The vaccine composition according to claim 1, wherein said PorA epitope is P1-20 and P1.9 and said FetA epitope is F3-1.

8. The composition according to claim 1, wherein said PorA epitope is P1,5-1, P1.2-2, P1.5-2, P1.16, P1.5, P1.10, P1.7, P1.7-2 or P1.4, and FetA epitope is F1-5, F5-1 or F3-9.

9. The composition according to claim 1, wherein said PorA epitope is P1.13-1, P1-20 or P1.9, and said FetA epitope is F3-1 or F5-5.

10. The composition according to claim 1, wherein PorA epitope is P1.19 or P1.15.

11. The composition according to claim 1, wherein said PorA epitope is P1.2, P1.19 or P1.15 and said FetA epitope is F1-7.

12. The composition according to claim 1, wherein said PorA epitope is P1.5 or P1.2, and said FetA epitope is F3-6 or F5-1.

13. The composition according to claim 1, wherein said PorA epitope is P1.7, P1.16, P1.19 or P1.15, and said FetA epitope is F3-1.

14. The composition according to claim 1, wherein said PorA epitope is P1.7-2 or P1.4, and said FetA epitope is F1-5 or F1-7.

15. The composition according to claim 1, further comprising one or more components selected from the group consisting of transferrin binding proteins, PorB, Opa and NspA.

16. The composition according to claim 15, wherein said further component is transferrin binding protein, PorB or Opa.

17. The composition according to claim 16, wherein said further component is Opa.

18. A method of inducing an immune response against *Neisseria meningitides* infection in a subject comprising administering to said subject an effective amount of the composition according to claim 1.

19. The composition of claim 1, wherein said purified FetA protein comprises a variable region having the amino acid sequence selected from SEQ ID NO: 19-23.

20. The composition of claim 1, wherein said composition comprises at least 6 of said PorA epitopes and 5 of said FetA epitopes.

21. The composition of claim 1, wherein said composition comprises no more than 6 of said PorA epitopes and no more than 5 of said FetA epitopes.

22. The composition of claim 2, wherein said purified epitopes are present in a liposome.

* * * * *

```
                      SEQUENCE LISTING

<160> NUMBER OF SEQ ID NOS: 23

<210> SEQ ID NO 1
<211> LENGTH: 12
<212> TYPE: PRT
<213> ORGANISM: Neisseria meningitidis

<400> SEQUENCE: 1

Pro Leu Pro Asn Ile Gln Pro Gln Val Thr Lys Arg
1               5                   10

<210> SEQ ID NO 2
<211> LENGTH: 12
<212> TYPE: PRT
<213> ORGANISM: Neisseria meningitidis

<400> SEQUENCE: 2

Pro Leu Gln Asn Ile Gln Pro Gln Val Thr Lys Arg
1               5                   10

<210> SEQ ID NO 3
<211> LENGTH: 15
<212> TYPE: PRT
<213> ORGANISM: Neisseria meningitidis

<400> SEQUENCE: 3

Ala Gln Ala Ala Asn Gly Gly Ala Ser Gly Gln Val Lys Val Thr
1               5                   10                  15

<210> SEQ ID NO 4
<211> LENGTH: 15
<212> TYPE: PRT
<213> ORGANISM: Neisseria meningitidis

<400> SEQUENCE: 4

Ala Gln Ala Ala Asn Gly Gly Ala Ser Gly Gln Val Lys Val Thr
1               5                   10                  15

<210> SEQ ID NO 5
<211> LENGTH: 15
<212> TYPE: PRT
<213> ORGANISM: Neisseria meningitidis
```

-continued

```
<400> SEQUENCE: 5

Gln Pro Gln Thr Ala Asn Thr Gln Gln Gly Gly Lys Val Lys Val
1               5                   10                  15

<210> SEQ ID NO 6
<211> LENGTH: 13
<212> TYPE: PRT
<213> ORGANISM: Neisseria meningitidis

<400> SEQUENCE: 6

Pro Leu Gln Asn Ile Gln Gln Pro Gln Val Thr Lys Arg
1               5                   10

<210> SEQ ID NO 7
<211> LENGTH: 14
<212> TYPE: PRT
<213> ORGANISM: Neisseria meningitidis

<400> SEQUENCE: 7

Pro Pro Ser Lys Ser Gln Pro Gln Val Lys Val Thr Lys Ala
1               5                   10

<210> SEQ ID NO 8
<211> LENGTH: 12
<212> TYPE: PRT
<213> ORGANISM: Neisseria meningitidis

<400> SEQUENCE: 8

Pro Leu Pro Asn Ile Gln Pro Gln Val Thr Lys Arg
1               5                   10

<210> SEQ ID NO 9
<211> LENGTH: 12
<212> TYPE: PRT
<213> ORGANISM: Neisseria meningitidis

<400> SEQUENCE: 9

Pro Leu Gln Asn Ile Gln Pro Gln Val Thr Lys Arg
1               5                   10

<210> SEQ ID NO 10
<211> LENGTH: 13
<212> TYPE: PRT
<213> ORGANISM: Neisseria meningitidis

<400> SEQUENCE: 10

Tyr Tyr Thr Lys Asp Thr Asn Asn Asn Leu Thr Leu Val
1               5                   10

<210> SEQ ID NO 11
<211> LENGTH: 13
<212> TYPE: PRT
<213> ORGANISM: Neisseria meningitidis

<400> SEQUENCE: 11

His Phe Val Gln Asn Lys Gln Asn Gln Arg Pro Thr Leu
1               5                   10

<210> SEQ ID NO 12
<211> LENGTH: 13
<212> TYPE: PRT
<213> ORGANISM: Neisseria meningitidis

<400> SEQUENCE: 12

Tyr Trp Thr Thr Val Asn Thr Gly Ser Ala Thr Thr Thr
```

```
<210> SEQ ID NO 13
<211> LENGTH: 13
<212> TYPE: PRT
<213> ORGANISM: Neisseria meningitidis

<400> SEQUENCE: 13

His Val Val Val Asn Asn Lys Val Ala Thr His Val Pro
1               5                   10

<210> SEQ ID NO 14
<211> LENGTH: 10
<212> TYPE: PRT
<213> ORGANISM: Neisseria meningitidis

<400> SEQUENCE: 14

Tyr Val Asp Glu Gln Ser Lys Tyr His Ala
1               5                   10

<210> SEQ ID NO 15
<211> LENGTH: 14
<212> TYPE: PRT
<213> ORGANISM: Neisseria meningitidis

<400> SEQUENCE: 15

His Phe Val Gln Gln Thr Pro Gln Ser Gln Pro Thr Leu Val
1               5                   10

<210> SEQ ID NO 16
<211> LENGTH: 13
<212> TYPE: PRT
<213> ORGANISM: Neisseria meningitidis

<400> SEQUENCE: 16

His Tyr Thr Arg Gln Asn Asn Ala Asp Val Phe Val Pro
1               5                   10

<210> SEQ ID NO 17
<211> LENGTH: 13
<212> TYPE: PRT
<213> ORGANISM: Neisseria meningitidis

<400> SEQUENCE: 17

His Phe Val Gln Asn Lys Gln Asn Gln Arg Pro Thr Leu
1               5                   10

<210> SEQ ID NO 18
<211> LENGTH: 14
<212> TYPE: PRT
<213> ORGANISM: Neisseria meningitidis

<400> SEQUENCE: 18

His Phe Val Gln Gln Thr Pro Lys Ser Gln Pro Thr Leu Val
1               5                   10

<210> SEQ ID NO 19
<211> LENGTH: 32
<212> TYPE: PRT
<213> ORGANISM: Neisseria meningitidis

<400> SEQUENCE: 19

Ser Gln Phe Lys Ile Glu Asp Lys Glu Lys Ala Thr Asp Glu Glu Lys
1               5                   10                  15

Asn Lys Asn Arg Glu Asn Glu Lys Ile Ala Lys Ala Tyr Arg Leu Thr
```

```
<210> SEQ ID NO 20
<211> LENGTH: 39
<212> TYPE: PRT
<213> ORGANISM: Neisseria meningitidis

<400> SEQUENCE: 20

Gly Glu Phe Ser Ile Pro Thr Lys Glu Lys Asn Gly Lys Glu Val
1               5                   10                  15

Asp Lys Pro Met Glu Gln Gln Lys Lys Asp Arg Ala Asp Glu Ala Thr
                20                  25                  30

Val His Ala Tyr Lys Leu Ser
            35

<210> SEQ ID NO 21
<211> LENGTH: 42
<212> TYPE: PRT
<213> ORGANISM: Neisseria meningitidis

<400> SEQUENCE: 21

Gly Glu Phe Glu Ile Ser Gly Lys Lys Lys Asp Pro Lys Asp Pro Lys
1               5                   10                  15

Lys Glu Ile Asp Lys Thr Asp Glu Glu Lys Ala Lys Asp Lys Lys Asp
                20                  25                  30

Met Asp Leu Val His Ser Tyr Lys Leu Ser
            35                  40

<210> SEQ ID NO 22
<211> LENGTH: 39
<212> TYPE: PRT
<213> ORGANISM: Neisseria meningitidis

<400> SEQUENCE: 22

Ser Lys Phe Ser Ile Pro Thr Thr Glu Lys Lys Asn Gly Gln Asp Val
1               5                   10                  15

Ala Lys Pro Ala Asp Gln Gln Ala Lys Asp Arg Lys Asp Glu Ala Leu
                20                  25                  30

Val His Ser Tyr Arg Leu Thr
            35

<210> SEQ ID NO 23
<211> LENGTH: 42
<212> TYPE: PRT
<213> ORGANISM: Neisseria meningitidis

<400> SEQUENCE: 23

Gly Lys Phe Lys Ile Ser Asp Lys Lys Pro Asp Pro Asn Asp Pro Thr
1               5                   10                  15

Lys Glu Ile Asp Lys Asp Ala Ala Glu Lys Ala Lys Asp Lys Lys Asp
                20                  25                  30

Met Asp Leu Val His Ser Tyr Lys Leu Ser
            35                  40
```